(12) United States Patent  (10) Patent No.: US 7,910,064 B2
Hamilton et al.  (45) Date of Patent: Mar. 22, 2011

(54) NANOWIRE-BASED SENSOR CONFIGURATIONS

(75) Inventors: James M. Hamilton, Sunnyvale, CA (US); Robert S. Dubrow, San Carlos, CA (US); Calvin Y. H. Chow, Portola Valley, CA (US)

(73) Assignee: Nanosys, Inc., Palo Alto, CA (US)

( * ) Notice: Subject to any disclaimer, the term of this patent is extended or adjusted under 35 U.S.C. 154(b) by 759 days.

(21) Appl. No.: 11/399,218

(22) Filed: Apr. 6, 2006

(65) Prior Publication Data

US 2009/0124025 A1 May 14, 2009

Related U.S. Application Data

(62) Division of application No. 10/853,006, filed on May 25, 2004, now abandoned.

(60) Provisional application No. 60/475,831, filed on Jun. 3, 2003.

(51) Int. Cl.
*G01N 27/00* (2006.01)

(52) U.S. Cl. ............... 422/82.01; 422/50; 422/82.02; 436/518; 436/524; 436/525; 435/4; 435/7.1; 435/283.1; 435/287.1; 435/287.2

(58) Field of Classification Search ........... 435/4, 7.1, 435/283.1, 287.1, 288.7, 287.2, 288.3; 422/50, 422/61, 82.01, 82.02; 436/518, 524, 525
See application file for complete search history.

(56) References Cited

U.S. PATENT DOCUMENTS

| | | | |
|---|---|---|---|
| 4,673,474 A | 6/1987 | Ogawa | |
| 4,939,556 A | 7/1990 | Eguchi et al. | |
| 5,089,545 A | 2/1992 | Pol | |
| 5,274,602 A | 12/1993 | Glenn | |
| 5,453,970 A | 9/1995 | Rust et al. | |
| 5,475,341 A | 12/1995 | Reed | |
| 5,589,692 A | 12/1996 | Reed | |
| 5,599,668 A * | 2/1997 | Stimpson et al. | 435/6 |
| 5,620,850 A | 4/1997 | Bamdad et al. | |
| 5,640,343 A | 6/1997 | Gallagher et al. | |
| 5,646,001 A * | 7/1997 | Terstappen et al. | 435/7.21 |
| 5,739,057 A | 4/1998 | Tiwari et al. | |
| 5,751,156 A | 5/1998 | Muller et al. | |
| 5,830,538 A | 11/1998 | Gates et al. | |

(Continued)

FOREIGN PATENT DOCUMENTS

EP  1087413  3/2001

(Continued)

OTHER PUBLICATIONS

Chen, J. et al. "Large On-Off Ratios and Negative Differential Resistance in a Molecular Electronic Device" Science (1999) 286:1550-1552.

(Continued)

*Primary Examiner* — Melanie Yu
(74) *Attorney, Agent, or Firm* — Donna M. Fabian (57) ABSTRACT

This invention provides nanowire based molecular sensors and methods for detecting analytes in a microfluidic system. Methods for sensing analytes include detecting changed electrical parameters associated with contact of a nanowire with the analyte in a microfluidic system. Sensors of the invention include nanowires mounted in microchambers of a microfluidic system in electrical contact with the detector, whereby electrical parameter changes induced in the nanowire by the analyte can be monitored by the detector.

22 Claims, 7 Drawing Sheets

U.S. PATENT DOCUMENTS

| | | | |
|---|---|---|---|
| 5,847,565 | A | 12/1998 | Narayanan |
| 5,858,862 | A | 1/1999 | Westwater et al. |
| 5,897,945 | A | 4/1999 | Lieber et al. |
| 5,903,010 | A | 5/1999 | Flory et al. |
| 5,942,443 | A | 8/1999 | Parce et al. |
| 5,997,832 | A | 12/1999 | Lieber et al. |
| 6,036,774 | A | 3/2000 | Lieber et al. |
| 6,038,060 | A | 3/2000 | Crowley |
| 6,060,724 | A | 5/2000 | Flory et al. |
| 6,069,380 | A | 5/2000 | Chou et al. |
| 6,123,819 | A | 9/2000 | Peeters |
| 6,128,214 | A | 10/2000 | Kuekes et al. |
| 6,143,184 | A | 11/2000 | Martin et al. |
| 6,149,819 | A | 11/2000 | Martin et al. |
| 6,203,864 | B1 | 3/2001 | Zhang et al. |
| 6,207,392 | B1 | 3/2001 | Weiss et al. |
| 6,256,767 | B1 | 7/2001 | Kuekes et al. |
| 6,286,226 | B1 | 9/2001 | Jin |
| 6,325,904 | B1 | 12/2001 | Peeters |
| 6,346,189 | B1 | 2/2002 | Dai et al. |
| 6,437,329 | B1 | 8/2002 | Yedur et al. |
| 6,528,020 | B1 | 3/2003 | Dai et al. |
| 6,643,165 | B2 | 11/2003 | Segal et al. |
| 6,843,902 | B1 | 1/2005 | Penner et al. |
| 7,163,659 | B2 * | 1/2007 | Stasiak et al. ............... 422/82.01 |
| 2001/0054709 | A1 | 12/2001 | Heath et al. |
| 2002/0117659 | A1 | 8/2002 | Lieber |
| 2002/0179434 | A1 | 12/2002 | Dai et al. |
| 2003/0054356 | A1 * | 3/2003 | Jacobson et al. .................. 435/6 |
| 2003/0089899 | A1 | 5/2003 | Lieber et al. |
| 2003/0134433 | A1 | 7/2003 | Gabriel et al. |
| 2003/0215816 | A1 | 11/2003 | Sundararajan et al. |
| 2003/0215865 | A1 | 11/2003 | Mayer et al. |
| 2004/0132070 | A1 * | 7/2004 | Star et al. .......................... 435/6 |
| 2004/0136866 | A1 * | 7/2004 | Pontis et al. .................... 422/57 |
| 2004/0188780 | A1 | 9/2004 | Kurtz |
| 2004/0210289 | A1 | 10/2004 | Wang et al. |
| 2005/0019842 | A1 * | 1/2005 | Prober et al. .................... 435/7.9 |
| 2005/0053525 | A1 | 3/2005 | Segal et al. |
| 2006/0054936 | A1 * | 3/2006 | Lieber et al. ................. 257/210 |

FOREIGN PATENT DOCUMENTS

| | | |
|---|---|---|
| WO | WO-9839250 | 9/1998 |
| WO | WO-9842620 | 10/1999 |
| WO | WO-0009443 | 2/2000 |
| WO | WO-0017101 | 3/2000 |
| WO | WO-0019494 | 4/2000 |
| WO | WO-0103208 | 1/2001 |
| WO | WO-0217362 | 2/2002 |
| WO | WO-0248701 | 6/2002 |
| WO | WO-03005450 | 1/2003 |

OTHER PUBLICATIONS

Chung, S-W. et al., "Silicon nanowire devices" Appl. Phys. Letts. (2000) 76:2068-2070.

Collier, C.P. et al., "Electronically Configurable Molecular-Based Logic Gates" Science (1999) 285:391-394.

Cui, Y. et al., "Functional nanoscale electronic devices assembled using silicon nanowire building blocks" Science (2001) 291:851-853.

Cui, Y. et al., "Nanowire nanosensors for highly sensitive and selective detection of biological and chemical species" Science (2001) 293:1289-1292.

Cui, Y. et al., "Diameter-controlled synthesis of single-crystal silicon nanowires" Appl. Phys. Letts. (2001) 78(15):2214-2216.

Cui, Y. et al., "Doping and electrical transport in silicon nanowires" J. Phys. Chem. (2000) 104(22):5213-5216.

Duan, X. et al., "General Synthesis of compound semiconductor nanowires" Adv. Materials (2000) 12(4):298-302.

Duan, X. et al., "Laser-assisted catalytic growth of singl crystal GaN Nanowires" J. Am. Chem. Soc. (1999) 122:188-189.

Duan et al., "Indium phosphide nanowires as bulding blocks for nanoscale electronic and optoelectronic devices" Nature (2001) 409:66-69.

Esfarjani, K. et al., "Electronic and transport properties of N-P doped nanotubes" Appl. Phys. Letts. (1999) 74:79-81.

Givargizov, E.I. "Fundamental aspects of VSL growth" J. Crys. Growth (1975) 31:20-30.

Gudikson, M.S. et al., "Diameter-selective synthesis of semiconductor nanowires" J. Am. Chem. Soc. (2000) 122:8801-8802.

Gudikson, M.S. et al., "Growth of nanowire supperlattice structures for nanoscale photonics and electronics" Nature (2002) 415:617-620.

Haraguchi, K. et al., "GaAs p-n junction formed in quantum wire crystals" Appl. Phys. Letts. (1992) 60:745-747.

Haraguchi, K. et al., "Polarization dependence of light emitted from GaAs p-n junctions in quantum wire crystals" J. Appl. Phys. (1994) 74(8):4220-4225.

Hiruma, K. et al., "Self-organized growth of GaAs/InAs heterostructure nanocylinders by organometallic vapor phase epitaxy" J. Chrys. Growth (1996) 163:226-231.

Huang, Y. et al., "Directed assembly of one-dimensional nanostructures into functional networks" Science (2001) 291:630-633.

Huang, Y. et al., "Logic gates and computation from assembled nanowire building blocks" Science (2001) 294:1313-1317.

Kanjanachuchai, S. et al., "Coulomb blockage in strained-Si nanowires on leaky virtual substrates" Semiconductor Science and Technology (2001) 16:72-76.

Kong et al., "Nanotube molecular wires as chemical sensors" Science (2000) 287:622-625.

Morales, A.M. et al., "A Laser Ablation Method for the Synthesis of Crystalline Seminconductor Nanowires" Science (1998) 279:208-211.

Padaste C. et al., "Modular amperometric immunosensor devices" Transducers 95 (1995) 2:487-490.

Tans, S.J. et al., "Room-termperature transistor based on a single carbon nanotube" Nature (1998) 393:49-52.

Tiefenauer, L.X. et al., "Toward amperometric immunosensor devices" Biosensors & Bioelectronics (1997) 12(3):213-223.

Wang, J. et al., "Highly polarized photoluminescence and photodetection from single indium phosphide nanowires" Science (2001) 293:1455-1457.

Wolf, W. et al., "Silicon processing for the VLSI era" Lattice Press 1:12-13 2000.

Wu, Y. et al., "Block-by-Block growth of single-crystalling Si?SiGe superlattice nanowires" Nanoletters (2002) 2(2):83-86.

Yamada, T., "Analysis of submicron carbon nanotube field-effect transistors" Appl. Phys. Letts. (2000) 76:628-630.

Yu, D.P. et al., "Nanoscale silicon wires synthesized using simple physical evaporation" Appl. Phys. Letts (1998) 72:3458-3460.

* cited by examiner

NANOWIRE-BASED SENSOR CONFIGURATIONS

CROSS-REFERENCE TO RELATED APPLICATION

This application is a divisional of U.S. patent application Ser. No. 10/853,006, filed May 25, 2004, which claims the benefit of U.S. Provisional Patent Application No. 60/475,831 filed Jun. 3, 2003, the full disclosures of which are hereby incorporated herein by reference in their entirety for all purposes.

STATEMENT AS TO RIGHTS TO INVENTIONS MADE UNDER FEDERALLY SPONSORED RESEARCH AND DEVELOPMENT

A portion of this invention was made under SBIR Grants from the National Institutes of Health, Grant Numbers 1 R43A152533-01 and 1 R43CA101567-01, and the government may have certain rights in the inventions.

FIELD OF THE INVENTION

The present invention is in the field of sensors for detection of analytes. The sensors of the invention can detect molecular species, e.g., in a chromatographic elution or in an array. Sensors of the invention are suitable for incorporation into analytical systems, including capillary based and microscale fluidic (or microfluidic) systems.

BACKGROUND OF THE INVENTION

Detectors used in analytical methods and screening protocols are often nonspecific, require complex chromogenic interactions, or are not well adapted to microscale systems. Analytical systems typically employ spectrophotometers, conductivity meters, pH meters, and the like, to detect elution of analytes from chromatographic separations. More specific detection of analytes often requires complex layered systems of affinity molecules, enzymes and substrates. Available detection systems often employ optical detection schemes for chemically labeled components which can suffer from excessive background signal, nonspecific signals, difficult data interpretation, analyte specific chemistry requirements, and the like.

Spectrophotometry can be useful to detect biological molecules in analytical systems. Proteins and nucleic acids have peak absorbances near the ultraviolet region for detection using photomultiplier tubes or photodiode array sensors. Such sensors can be blanked (set to zero) with analytical buffer in the flow cell. As the biological molecule elutes from a chromatographic separation (such as ion exchange, RP-HPLC, SEC, and the like) and flows into the flow cell, an absorbance peak can be detected by a spectrophotometer. Such spectrophotometric detection is generally nonspecific, can be expensive, and often yields relatively high signal to noise ratios, particularly when detecting very small concentrations of analyte.

Spectrophotometry can also be used to identify specific molecules in arrays or chromatographic eluates. In one common format, a biologic molecule is bound to a molecule with specific affinity (such as an antibody, lectin, receptor, or the like) which is also bound to a detectable marker (such as a radionuclide, an enzyme, or a fluorescent tag). The complex "sandwich" of bound molecules can be specifically detected by spectroscopic instruments. These affinity based systems can provide specific detection of molecules, but in addition to the above-mentioned difficulties, can also require the use of hazardous materials and complex plumbing for assay automation.

Conductivity and pH meters are commonly used to monitor chromatographic processes and analytical elutions. Such detectors can be configured to work in processing equipment, analytical instrumentation, or microfluidic devices to monitor the passage of charged molecules or buffer solutions. These detectors are typically not useful in detection of biological molecules for lack of specificity and sensitivity. In addition, the high impedance required for many of these detectors to sense changes in microenvironments can provide a noisy signal with poor sensitivity.

Biosensors have been described in which a mass of bound analyte molecules can change the resonant vibration frequency of a micro beam. In U.S. Pat. No. 6,303,288, Integrated Microchip Genetic Testing System, to Furcht, for example, molecular binding sites are located on the surface of a microbeam with a known vibration frequency. When molecules bind to the sites, the mass of the microbeam increases, reducing the vibrational frequency of the microbeam. Such vibrations can be induced and detected, e.g., as voltage potentials associated with a piezo-electric microbeam component. Another aspect of Furcht is detection of mechanical stress on an underlying piezoelectric element when analytes load onto the binding sites. Beam style piezoelectric detection devices require a complex multilayered etching and coating technology, produce microscale (but not nanoscale) sensor elements, and can have a disadvantageous ratio of binding surface to sensor mass.

Chemical sensors have also been described that employ binding agents on the surface of a semiconductor channel that connects a source and drain electrode. The binding of large amounts of charged analyte to the surface of the channel cases an electric field induced gating of the channel. While such chemically sensitive field effect transistors (or ChemFETs) have shown some functionality, the requirement of very large concentrations of charged analyte to achieve a detectable gating of the transistor has resulted in their not being particularly useful for most applications. Lieber et al., recently reported a ChemFET (see U.S. Patent Application number 2002/0117659, "Nanosensors", and Published International Patent Application number WO 02/48701, each of which is incorporated herein by reference in its entirety for all purposes) operating on the same basic principles, but which employs a semiconductor nanowire as the channel component. These nanoChemFETs reportedly have dramatically increased sensitivity as compared to the previously reported ChemFETs theoretically as a result of their substantially increased surface area to volume or cross-section ratio, e.g., providing a much larger binding region with a much smaller channel cross-section that is to be gated by the binding event. Despite these reported advances, there are a number of areas that would be ripe for improvement of ChemFET and nanoChemFET based devices and systems.

In particular, there remains a need for microsensors and/or nanosensors, as well as methods of utilizing such sensors, that combine the sensitivity of nanoChemFET based sensors with the robustness and data reliability of more conventional systems. The present invention provides these and other features which will be apparent upon complete review of the following.

SUMMARY OF THE INVENTION

The methods and sensors of the present invention provide, e.g., detection of analytes using nanowire sensors. Nanowire sensors of the invention include, e.g., nanowires mounted in chambers and in electrical contact with electrical parameter detectors that can signal the presence of an analyte. In accordance with the methods devices and systems of the invention, sensing of analyte molecules typically comprises detecting a change in an electrical parameter associated with a nanowire mounted in a chamber, in response to contact with the fluid containing the analyte. The change in the parameter can be the result of electrical gating of the nanowire resulting from analyte binding thereto, e.g., as in a NanochemFET configuration, or may result from other forces acting upon the wire, such as physical stress applied to the wire as a result of analyte binding.

Nanowire-based molecular sensors of the invention typically include, e.g., a nanowire mounted in a chamber, and an electrical parameter detector (e.g., a voltmeter, ohm meter, or ammeter) in electrical contact with the nanowire so as to detect an electrical characteristic or parameter of the wire, whereby the presence of an analyte can induce a detectable change in an electrical parameter associated with the nanowire. The chamber can be, e.g., a well, a channel, a capillary, a cell, or another similar vessel, microchannel, microcell, and/or the like. The chamber can be in fluid communication with an outlet flow from a column or channel of separation media to detect separated analytes, or can exist as a discrete element into which analyte containing fluid is deposited. The nanowires can be any of a variety of nanowire elements including, e.g., inorganic semiconductor nanowires, carbon or inorganic semiconductor nanotubes, or, in some cases, metallic nanowires. The nanowires can be, e.g., semiconductors in electrical circuits, and/or nanowires that exert influence on semiconductors in electrical contact with detectors. Electrical parameters monitored by the detectors can include, e.g., electrical resistance, voltage, and/or current. The analyte can induce a detectable electrical parameter change by, e.g., exerting a field effect on a nanowire sensor, nonspecifically binding to a nanowire, and/or specifically binding to nanowire. The chamber can be virtually any fluidic vessel suitable for receipt of fluid containing the analyte including, e.g., a microchamber, such as a microchannel or microcell within a microfluidic chip.

Specific molecular binding sites on nanowires for analytes can be, e.g., nucleic acids, peptide nucleic acids, peptides, antibodies, receptors, lectins, charged groups, chelators, and/or the like. Analytes detected by the nanowire based molecular sensors of the invention can include, e.g., nucleic acids, antigens, antibodies, proteins, ions and/or the like. A molecular array of analytes can be included in the microfluidic system of the invention, e.g., to provide high throughput screening.

In one aspect of the invention, the nanowire can be mounted to a piezojunction. The nanowire can be a semiconductor wire, or carbon based nanotube, with adequate tensile strength and/or rigidity to transfer physical stresses to the piezojunction. In the piezojunction embodiment, the nanowire can have, e.g., molecular binding sites for the analyte. The chamber can be a channel with a flowing fluid, so that, e.g., binding of the analyte to the binding sites increases the hydrodynamic drag of the fluid on the nanowire, resulting in stress and a detectable change in the electrical parameter at the piezojunction (typically detectable as a changed electrical parameter in a circuit through the junction). The chamber can be, e.g., a channel with a constriction where the nanowire is mounted to accelerate fluid flow at the site of the nanowire sensor. The constriction can be, e.g., caused by a buildup of analyte molecules at binding sites on the channel surface.

In some embodiments, the nanowire can be, e.g., a semiconductor, such as, e.g., a carbon nanotube, field effect sensitive doped semiconductor such as silicon, or piezoresistive doped silicon. As analytes bind to the nanowire at molecular binding sites, the diameter can increase along with the hydrodynamic stress exerted by the flowing fluid. The stress can cause a detectable increase the resistance in the in the piezoresistant nanowire. In some cases, the sensitivity of the system can be increased by providing a constriction in the microchannel where the nanowire is mounted.

In other embodiments, the nanowire can have, e.g., a resistance responsive to field effects. For example, the nanowire can be the gate region of a transistor so that binding of charged analytes to molecular binding sites on the nanowire detectably changes the electrical resistance of the nanowire (i.e., changes the ability of the nanowire to carry current). Alternately, the nanowire can be in close proximity to a gate region of a transistor (i.e., close enough for charges associated with the nanowire to exert field effects on the transistor). Detectable field effects can result, e.g., from specific binding of a charged molecule to the nanowire, nonspecific binding of a charged molecule to the nanowire, the presence of unbound charged molecules near the nanowire (i.e., near enough to exert field effects on the nanowire or an associated field effect transistor gate), and/or an applied voltage across the length of a channel where the nanowire is mounted. Background noise can be lowered in field effect embodiments, e.g., by turning off electrical currents in the chamber while measurements are being taken, and/or by lowering the ionic strength of solutions before detecting a change in the electrical parameter.

Nanowires of the molecular sensors can be fabricated and mounted in various ways, as appropriate for particular embodiments. The nanowire can be treated to block or remove charged surface groups to prevent background noise from exchange of ions or nonspecific blinding of charged molecules. The nanowires can have a length, e.g., between about 50 um and about 100 um, or a diameter between about 5 nm and 10 nm. Two or more nanowires can be mounted in the chambers to provide, e.g., controls, references, multiple analyses, extended quantitative range of analyses, and/or the like. The two or more nanowires can be, e.g., separate sections of a source nanowire to increase consistency in comparisons between the wires. Sensitivity of comparisons between nanowires can be improved by using a Wheatstone bridge in the detection circuit.

The local presence or surface binding of analytes can change electrical parameters associated with nanowires in sensors of the invention. The electrical parameters can include, e.g., voltage, resistance, and/or current. In certain cases where analyte binding progresses slowly, it can be difficult to accurately detect changes in the electrical properties of the wire resulting from binding, due to its low level of change per unit time. As such, detection of changed electrical parameters resulting from these chemical interactions can be enhanced, e.g., by monitoring the parameters before, during, and/or after the analyte is rapidly removed (relative to the binding time) from the binding sites. Because removal of material from binding sites can be affected much more rapidly than ordinary binding reactions that are often limited by diffusion kinetics (in addition to binding kinetics), it will result in a much more drastic and immediate shift in the electrical parameters of the wire that are associated with the analyte being bound to that surface, thus providing a much more pronounced shift per unit time. Rapid removal of the analyte can result from, e.g., exposure of the nanowire to a releasing energy or chemistry, e.g., via exposure to ultraviolet light, heat, an enzyme, a wash solution, an electrical current, and/or the like, as appropriate.

The methods of the invention can include, e.g., sensing of analyte molecules by mounting a nanowire in a chamber in electrical contact with an electrical parameter detector, contacting the nanowire with a fluid containing the analyte, and detecting a change in an electrical parameter associated with the nanowire. The electrical parameters detected in the methods can include, e.g., voltage, resistance, and/or current. The chamber can be, e.g., a microchamber in a microfluidic device.

Mounting the nanowire can include, e.g., etching the nanowire into a surface, settling the nanowire onto a surface of the chamber, flow orientation of the nanowire, micromanipulation, and/or growing the nanowire from a seeded surface.

In some embodiments, the nanowire can have piezoresistance and/or be functionally mounted to a piezojunction. In such a case, a fluid containing an analyte can flow through the microchamber, binding of the analyte to binding sites on the nanowire can increase hydrodynamic drag, and a detectable change in the electrical resistance can be generated in the nanowire.

In some environments, the nanowire can have an electrical resistance responsive to field effects. In such case, the field effect can result from, e.g., specific binding of a charged molecule to the nanowire, nonspecific binding of a charged molecule to the nanowire, the presence of unbound charged molecules near the nanowire, or an applied voltage across a length of a channel containing the nanowire. In many embodiments, the nanowire can have molecular binding sites for the charged analyte.

As noted above, in some embodiments of the methods, the sensitivity and/or range of analysis can be enhanced by, e.g., removing the analyte from the binding sites before or during detection of the changed electrical parameter. Such removal of analyte can result from, e.g., exposing the nanowire to ultraviolet light, heat, an enzyme, a wash solution, or an electrical current. In particular, because the binding of an analyte to the nanowire affects an electrical property of a wire, the removal of the bound analyte should have, e.g., substantially an equal but opposite effect on that property. Further, because one can generally cause the removal by applying a particular removal energy or chemistry, e.g., enzyme treatment, heat, electrical energy, UV energy, or washing with denaturant, one can generally force the dissociation at a much greater rate than occurs with binding. Specifically, the binding rate of analytes to ligands on a surface is typically limited by both the binding kinetics of the two molecules and the rate of diffusion of the analyte to the surface. In relatively large chambers, e.g., µl size vessels, such diffusion can be very slow to achieve maximal binding from one to tens of hours. Over such lengthy binding times a great number of variables can shift, e.g., temperature, ionic strength of buffers, etc, yielding potential variations in electrical signal that can interfere with accurate measurement of the binding event. By rapidly removing the analyte, however, one can sense the change in the electrical parameter of the wire that is associated with the presence (or absence) of the analyte being bound thereto and can do so much more rapidly, e.g., on the order of seconds or milliseconds. The result is that a significant number of interfering events can be effectively eliminated from having an impact on the measurement.

In other embodiments, such as in methods involving DNA hybridization or field effects of analytes, sensitivity, specificity, and/or quantitative range can be enhanced, e.g., by washing the nanowire with a low ionic strength solution before detecting the change in the electrical parameter. The sensitivity and accuracy of the methods can be enhanced, e.g., by comparing the electrical parameter change associated with a test nanowire to an electrical parameter associated with a control nanowire. In methods for detection of analytes eluting from an electrophoretic separation, e.g., detection of changed electrical parameters can be enhanced by shutting off electrophoretic current before detecting a change.

Analytes detected in methods of the invention can affect the nanowire electrical character by electric field effects. The field effects can originate from, e.g., local charged analytes, analyte products, specific binding or charged analytes, and/or nonspecific binding or charged analytes. Exemplary analytes detected by the methods can include, e.g., nucleic acids, antigens, antibodies, proteins, ions, and/or the like. In embodiments where analytes are bound to nanowires, e.g., binding sites can include nucleic acids, peptide nucleic acids, antibodies, receptors, lectins, charged groups, and/or chelators.

Definitions

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a surface" includes a combination of two or more surfaces; reference to "media" includes mixtures of media, and the like.

Unless defined otherwise, all technical and scientific terms used herein have the same meaning as commonly understood by one of ordinary skill in the art to which the invention pertains. Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

The term nanoscale, as used herein, refers to objects and components on a nanometer scale. For example, nanowires can range in diameter from about 0.1 nm to about 1000 nm.

The term electrical parameters associated with nanowires, as used herein, refers changes in a voltage, current, and/or resistance detectable by a detector in electrical contact with the nanowires or in contact with circuits influenced by physical or electrical effects from the nanowires.

The term chamber, as used herein, refers to a confined space with at least one surface to control fluid flow, e.g., chambers, conduits, i.e., channels, capillaries or tubes, wells, cells, vessels, microchannels, microcells, and/or the like.

The phrase "operably coupled" as used herein, means that two components are connected so as to perform their relative functions with respect to each other. For example, an electrical circuit that is operably coupled to a detector is typically electrically connected such that signals from the detector are passed through the circuit. Similarly, a fluidic channel that is operably coupled to a sensor is provided in sufficient contact or communication that the sensor can sense what is deposited in the channel. Further, and without limiting the definition, an energy source may be operably coupled to another component, such that energy is delivered to and capable of use or exploitation by the other component. One of skill in the art will readily recognize that operable couplings will vary depending upon the context of the phrase.

DETAILED DESCRIPTION

Nanowire-based sensor configurations of the invention provide, e.g., sensors and methods to detect analytes in process, analysis, and/or microfluidic systems. The sensors can be, e.g., nanowires mounted in chambers and in electrical contact with electrical parameter detectors for detection of changes in the nanowire electrical properties on interaction with an analyte. The methods for sensing analytes can include, e.g., contacting a nanowire mounted in a chamber of a microfluidic system with an analyte, and detecting a change in an electrical parameter associated with the nanowire to sense the analyte. The sensors and methods of the invention can be used, e.g., to detect analytes of interest in chromatographic separations and/or sample cells of microarrays.

Nanowire-Based Sensors

The sensors of the invention include, for example, nanowires mounted in chambers of devices wherein the presence of an analyte of interest induces a detectable change in an electrical parameter associated with the nanowires. The chamber can be in fluid communication with an outlet flow from a column or channel of separation media to monitor elution of analytes. The chambers can be, e.g., channels, cells, vessels, microchannels, or sample cells of a microarray, where the analyte can interact with the nanowire physically or electrically to affect a voltage, resistance, or current associated with the nanowire. The nanowires can, e.g., interact with a piezojunction, exhibit electric field effects, or piezoresistance, to provide the detectable changes in electrical parameters in response to the analyte interactions. The nanowires can be mounted, e.g., to chamber surfaces in electrical contact with suitable detector systems.

Figure 1A:
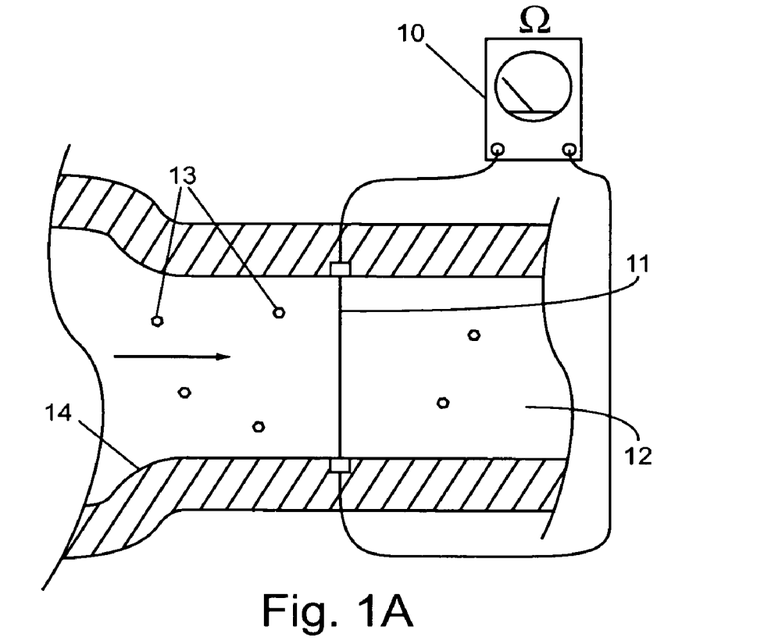
FIGS. 1A and 1B are schematic diagrams of a nanowire-based analyte sensor working in a piezoresistive configuration.
Figure 1B:
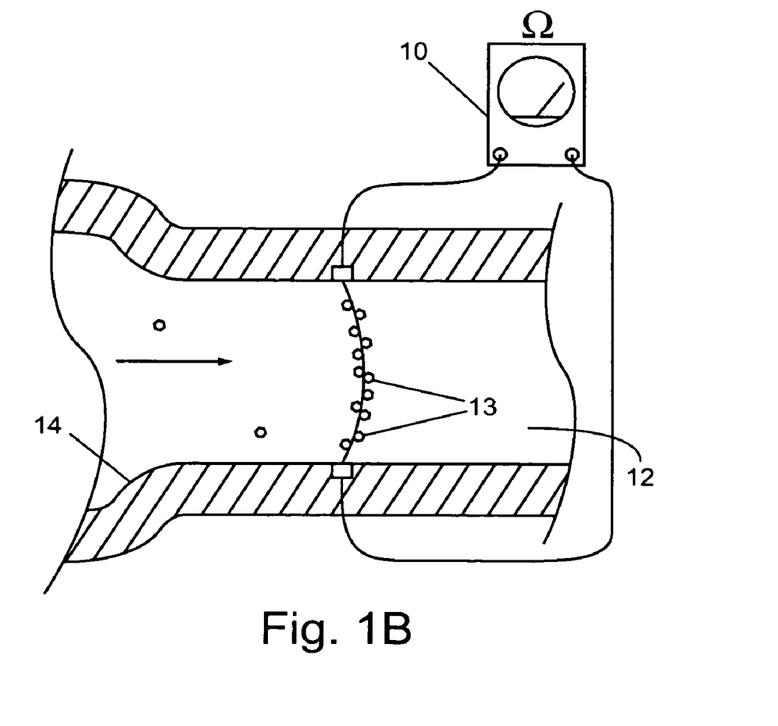

In one embodiment, as shown in FIG. 1A, one or more detectors 10 (an ohm meter) is in electrical contact with piezoresistive nanowire 11 that is mounted across a stream of flowing fluid in channel 12 (a chamber of the invention). The nanowire has surface binding sites that can capture particular analytes 13 from the fluid, thus increasing the diameter of the nanowire. As the diameter increases, the physical stress from hydrodynamic drag on the nanowire increases to change the electrical resistance ($\Omega$) of the nanowire, as shown in FIG. 1B. The change of resistance in the nanowire can be detected and correlated to the presence and/or amount of analyte in the fluid stream.

Figure 2A:
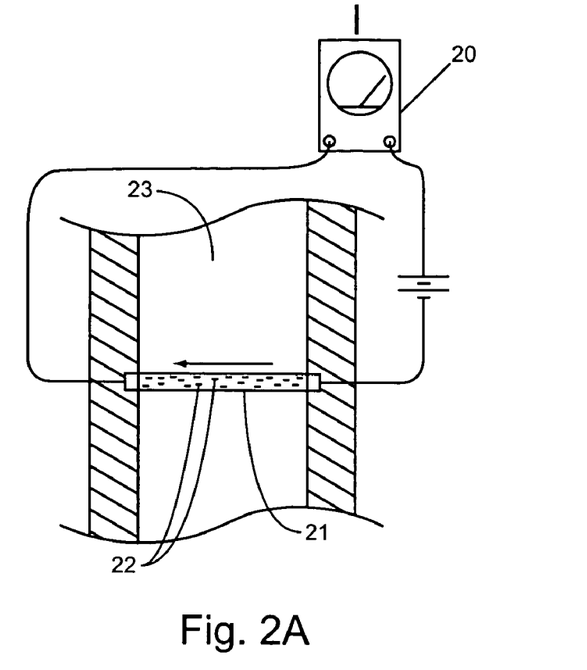
FIGS. 2A and 2B are schematic diagrams of a nanowire-based analyte sensor working in a field effect configuration.
Figure 2B:
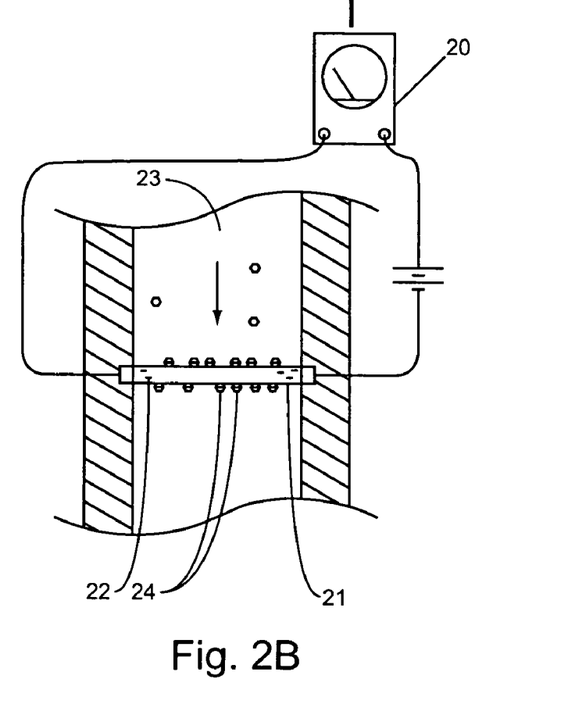

In another embodiment, as shown in FIG. 2A, one or more detectors 20 (an amp meter) is in electrical contact with nanowire 21 having electric current carriers 22 sensitive to electrical field effects (i.e., the nanowire can carry less electrical current in the presence of certain electrical fields). With the nanowire exposed to fluid in chamber 23, the presence or binding of charged analyte 24 can repel carriers to cause a detectable reduction in current (I) flow through the nanowire, as shown in FIG. 2B. As will be appreciated, where comparative nanowires, or duplicative nanowires are employed in a given system, one or more detectors may be used to differentially or duplicatively measure the electrical parameters of these nanowires.

Nanowires

Nanowires of the invention can be, e.g., nanoscale structures that can be mounted to chambers to functionally interact with selected analytes and detectors of the invention. The nanowires can be, e.g., beams, fibers, tubes, wires, and the like, of any length but having a nanoscale width and/or thickness. The nanowires can be manufactured by any methods known in the art from any suitable material. For example, in some preferred aspects, the nanowires used in the invention are fabricated using metal catalyst mediated vapor/liquid-solid (VLS) growth processes, e.g., as described in Published International Patent Application Nos. WO 02/17362, WO 02/48701, and 01/03208, using colloidal gold or other metal catalysts, or Greene et al. ("Low-temperature wafer scale production of ZnO nanowire arrays", L. Greene, M. Law, J. Goldberger, F. Kim, J. Johnson, Y. Zhang, R. Saykally, P. Yang, Angew. Chem. Int. Ed. 42, 3031-3034, 2003, using thin film metal catalysts, or through the use of PECVD, which employs synthesis temperatures of approximately 200° C. Such methods can be readily employed to produce nanowires of any of a variety of different materials, including Group III-V, Group II-VI and Group IV semiconductors. A wide variety of such semiconductor materials may be used for nanowires and nanoribbons in accordance with the invention, including semiconductive nanowires or nanoribbons, that are comprised of semiconductor material selected from, e.g., Si, Ge, Sn, Se, Te, B, C (including diamond), P, B—C, B—P (BP6), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, BeSiN2, $CaCN_2$, $ZnGeP_2$, $CdSnAs_2$, $ZnSnSb_2$, $CuGeP_3$, $CuSi_2P_3$, $(Cu, Ag)(Al, Ga, In, Tl, Fe)(S, Se, Te)_2$, $Si_3N_4$, $Ge_3N_4$, $Al_2O_3$, $(Al, Ga, In)_2 (S, Se, Te)_3$, $Al_2CO$, and an appropriate combination of two or more such semiconductors.

In certain aspects, the semiconductor may comprise a dopant from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; or an n-type is selected from a group consisting of: Si, Ge, Sn, S, Se and Te.

Additionally, the nanowires or nanoribbons can include carbon nanotubes, or nanotubes formed of conductive or semiconductive organic polymer materials, (e.g., pentacene, and transition metal oxides).

Hence, although the term "nanowire" is referred to throughout the description herein for illustrative purposes, it is intended that the description herein also encompass the use of nanotubes (e.g., nanowire-like structures having a hollow tube formed axially therethrough). Nanotubes can be formed in combinations/thin films of nanotubes as is described herein for nanowires, alone or in combination with nanowires, to provide the properties and advantages described herein.

Furthermore, it is noted that a thin film of nanowires may be employed in the context of the present invention, and that such thin film may comprise a "heterogeneous" film, which incorporates semiconductor nanowires and/or nanotubes, and/or nanorods, and/or nanoribbons, and/or any combination thereof of different or similar composition and/or structural characteristics. For example, a "heterogeneous film" can includes nanowires/nanotubes with varying diameters and lengths, and nanotubes and/or nanotubes that are "heterostructures" having varying characteristics.

Such individual nanowires may be compositionally homogeneous or they may include heterostructures where a single nanowire possesses regions that are comprised of different materials. Such regions may be longitudinally distinct, e.g., one segment of nanowire of a first material joined to another segment of nanowire of a second material, or they may be coaxially oriented, e.g., a core of a first material surrounded by a shell of a second material.

Sensors of the invention can include, e.g., nanowires mounted in chambers of a device substantially exposing the nanowire surface to chamber fluids while making electrical contact with detector associated circuits. The nanowires can have any appropriate length but have a width and/or thickness ranging, e.g., from less than about 1 um to about 1 nm, or from about 20 nm to about 5 nm, or about 10 nm. The nanowires can have piezoelectric or field effect properties, or a functional association with a piezo junction or field effect transistor gate.

The nanowire components integrated into the sensor devices and systems of the invention may be deposited in place between, e.g., a source and drain electrode, or they may, in some instances be grown in situ, e.g., using a ohmic contact pad as the substrate for nanowire synthesis. Alternatively, a nanowire or nanoribbon component may be fabricated using more conventional lithographic processes, e.g., as described in Published International Patent Application No. WO 2004/003535, which is incorporated herein by reference in its entirety for all purposes can be fabricated, for example, by photolithography, e-beam lithography, and/or focused Ion beam (FIB) lithography. In this embodiment, the nanowire can be fabricated, e.g., as an integral component during lithography of a microfluidic device. In photolithography, a substrate can be etched according to the pattern of a mask, as is known by those skilled in the art. For example, a layer of photoresist can be applied to the substrate, the photoresist exposed to a light source through a mask pattern, and the pattern disclosed by chemical dissolution of any photoresist not protected in the shadow of the mask. The patterned substrate can be etched by application of chemical etchants to the disclosed surfaces. A nanowire can remain, e.g., as the photoresist or as substrate protected from the etchant by the photoresist.

The nanowires of the invention can be grown, e.g., from sites seeded on a substrate. For example, a wafer of silicon, or another substrate, can be sprinkled or sputtered with nanometer-scale gold particles and exposed to a vapor of a semiconductor material in a furnace. The semiconductor can dissolve into the gold particles and crystallize between the substrate and particle. A shaft of semiconductor crystal, about the same diameter as the particle, can grow up from the substrate. The wires can be, e.g., 100 times, 1000 times, or more longer than their diameter. Shaft diameters and crystal structure can be quite uniform along the length of a single (source) wire. Dopants can be added, adjusted, and changed in the vapor to control amount and type of carriers in the semiconductor nanowire as it grows.

Nanowires can be fabricated from any material providing suitable physical and/or electrical properties for sensors of the invention. Resistance of many conductors changes in response to physical stresses (piezoresistance). Many semiconductors are known to exhibit a relatively high degree of piezoresistance. In many embodiments, sensors respond to physical stresses of analyte binding by changing electrical parameters. The nanowire can be strong enough to withstand the stress while the electrical resistance changes in response to the stress. In another aspect, tensile stress is placed on an analyte loaded nanowire and the stress is transferred to a piezojunction of a transistor where the nanowire is mounted. The voltage or current transmitted through the transistor can vary according to the stress on the nanowire. In such a sensor, strength of the nanowire and junction mount can be more important aspects of the sensor than the piezoresistance properties of the nanowire.

In other embodiments, sensors provide changed electrical parameters in response to electrical fields (field effects). Field effect sensors can be configured so that the nanowire does not experience undue stress. Nanowires employed in field effect sensors are typically doped semiconductors. Dopants can provide n-type and/or p-type carriers in the semiconductor. N-type dopants can be impurities, such as arsenic, with 5 valence electrons which can contribute 4 electrons to the silicon crystal structure with one electron left over to carry current. P-type dopants can be impurities, such as gallium, with 3 valence electrons which can contribute only 3 electrons to the silicon crystal structure, thereby leaving a "hole" in the crystal structure capable of carrying electrical current. Field effects can occur, for example, when an electric field from a negatively charged molecule repels carrier electrons from a nearby n-type semiconductor reducing the capacity of the semiconductor to carry a current.

In some aspects of the sensors of the invention, binding sites for analytes of interest can be incorporated onto nanowires. The binding sites can be relatively nonspecific, such as, e.g., charged groups, hydrophobic, or chelating groups on the nanowire surface. The binding sites can have specific affinity for certain analytes, such as in the case of nucleic acids, pDNA, peptides, antibodies, receptors, lectins, and the like. Charged groups, hydrophobic groups, and/or chelating groups can be incorporated into nanowires during fabrication, e.g., in a photoresist or semiconductor vapor. Optionally, the groups can be added to the nanowire surface, e.g., by reaction chemistries with substrate or application of a coating material to the nanowire. Specific affinity molecules can be bound to the surface of nanowires through the use of linker chemistries. For example, dopants, substrate molecules, or applied coatings can provide linker reactive groups, such as amines, sulfhydryls, carboxylic acids, alcohols, aldehydes, and thiols, that can covalently bond to commercially available bivalent linker molecules. Binding groups can be cross-linked to nanowires using linkage chemistries including bivalent linker chains having terminal hydroxysuccinimide (reactive with primary amines), maleimides, haloacetyls, pyridyl disulfides (reactive with sulfhydral groups), hydrazines (reactive with aldehydes), ethyldiethylamino propylcarbodiimide (EDC, reactive with carboxyl groups).

To avoid nonspecific background noise in some sensors of the invention, titratable and reactive groups on the nanowire surface can be blocked or removed. For example, charged groups on the nanowire surface can be titrated with changes in pH during an analysis causing changed field effects or voltage changes. In another example, unwanted charged groups on the nanowire surface can nonspecifically bind oppositely charged molecules from the surrounding fluids to generate false positive signals. Charged, titratable, and reactive groups can be blocked or removed by methods appreciated by those skilled in the art. For example, exposed silicates can be blocked with silane groups, or affinity binding can take place in blocker solutions. Alternatively, metal layers, e.g., gold and/or self assembling monolayers may be used to block surface charges of the native silicon (see, e.g., U.S. Provisional Patent Application No. 60/426,076, filed Nov. 13, 2002, and incorporated herein in its entirety for all purposes).

Nanowires can be mounted to microchambers of microfluidic systems, e.g., to sense the presence of analytes of interest. Mounting, as discussed in greater detail in the Methods section below, can include, e.g., etching a nanowire as an integral part of a chip, growing a nanowire from the surface of a chip, growing a nanowire from a transistor gate, randomly settling nanowires in a solution onto contacts, using flow orientation techniques, masking to direct nanowires onto contacts, micromanipulation, and/or the like. Typically, nanowires in sensors of the invention are mounted between detector electrical contacts on the surface of microchambers to provide nanowire surface interaction with flowing or incubating fluids and analytes. In a piezoresistive configuration, as shown in FIG. 1, the nanowire can be, e.g., mounted between channel walls 14 perpendicular to the flow of fluids. In this configuration, a constriction in the microchannel can increase sensitivity by accelerating fluid flow. In a field effect configuration, the nanowire can be mounted, e.g., suspended across a chamber in any orientation, or in contact with a chamber wall (e.g., when acting as a back gate to a field effect transistor mounted in the wall).

Microfluidic Systems

Sensors of the invention can be well suited to detection of analytes in microfluidic devices. Such microfluidic devices can be, e.g., an analytical instrument or a screening system having one or more component with microchannels or microcells. Microfluidic devices generally include, e.g., a chip of substrate material fabricated with microscale fluid handling elements. The chip can be associated with other system components, such as, e.g., robotic systems, computer systems, molecular libraries, detector devices, environmental control systems, and/or the like.

In one embodiment, microfluidic devices can include robotic application of samples from a molecular array to an analytical microfluidic chip. For example, a library of molecules can be stored on microwell plates which can be robotically transferred to a stage for sampling. A robotic sipper or pipettor can receive samples from the microwells and transfer them in series or parallel to microcells on the microfluidic chip. The microcells can be in fluid contact with microchannels in the chip so that samples can be inserted into flow streams of buffers and/or reagents in the microchannels. The samples can be introduced into microscale protocols, such as chromatographic separations, affinity binding, molecular amplification, and the like, in the microchannels or microcells. Detectors (e.g., of the present invention) associated with the channels or cells can identify and/or quantify molecular species of interest and transmit the data to a computer system for interpretation and storage.

The microfluidic chip can include, e.g., a solid substrate with an embedded pattern of microchambers. The substrate can be formed from materials such as, e.g., glass, ceramic, semiconductor, layered films, metal, plastic, and/or the like. The microchambers can be, e.g., microwells, microchannels, microcells, and/or the like, in which samples, buffers, and/or reagents are held or transported. For example, samples held in microwells can flow, by differential pressure or electroosmotic flow, through chromatographic media in a microchannel before incubation with chromogenic reagents in a microcell. Microchannels can be, e.g., etched, machined, molded, and/or the like, into the substrate to form channels of any length, with widths and/or depths ranging from less than about 1 mm to less than about 10 um, or from about 10 um to about 0.1 um, or less.

The microfluidic chip can have conduit and/or electrical connections to outside devices, e.g., to provide power, fluids, and/or data transfer. The chip can have ports to receive conduit manifolds for provision of flow driving pressures or introduction of fluids, such as samples, buffers, and/or reagents. The chip can have electrical contacts and circuits for provision of voltage potentials to electrophoretic media, voltages for electroosmotic flow and control, voltages for microcell temperature controllers, data transmission between sensors and computers, and/or the like.

Electrical Parameter Detectors

Detectors in the sensors of the invention can detect changes in electrical parameters associated with nanowires in response to interactions with analytes of interest. Detectors of the invention include, e.g., volt meters, ammeters, and/or ohm meters to measure changes in voltages, current, and/or resistance associated with the nanowires. The detectors can be, e.g., in electrical contact with the nanowires or associated electronic components to detect binding or the presence of analytes. Detectors can monitor nanowires and/or associated electronic components configured, e.g., with piezoresistive nanowires (see, FIG. 1), nanowires mounted to piezo junctions (see, FIG. 4), field effect nanowire conductors (see, FIG. 2), nanowires mounted as field effect transistor back gates, and/or field effect nanowires mounted in microchannels between direct current voltage electrodes (see FIG. 3).

Analytes can be bound to nanowires, e.g., to exert physical stress and/or field effects on nanowire sensors of the invention. Binding can be specific and/or non specific. Specific binding can be, e.g., affinity binding, such as the "lock and key" style interactions common in biological molecules including, e.g., nucleic acid hybridizations, antibody/antigen binding, cell membrane receptor/signal molecule interactions, lectin binding, and/or the like. Nonspecific binding can include, e.g., more generalized molecular interactions, such as, e.g., attraction between oppositely charged molecules, interaction of hydrophobic molecules, chelation of metal ions, and/or the like. A nonspecific interaction can be, e.g., binding of negatively charged nucleic acids to a positively charged solid support material, such as an anion exchange resin. Binding of analytes is necessary to detection in many piezoelectric configured sensors of the invention. Binding can provide close proximity beneficial to, e.g., detection sensitivity or specificity in many field effect configured sensors of the invention.

Analytes can be detected by, e.g., the physical stress and/or field effects they impose on nanowires of the sensors. Analytes of the invention can include, e.g., biological molecules and charged molecules, such as nucleic acids, antigens, antibodies, proteins, ions, and/or the like. The analytes can bind specifically or nonspecifically onto binding sites on the surface of nanowires, e.g., causing stress on piezoresistive materials which elicit resistance changes detectable by an ohm meter. Charged analytes (including, e.g., nucleic acids, ions, and many proteins) can affect carrier density in nanowires, or associated electronic components, through the influence of electric lines of force. Uncharged analytes can be detected indirectly by detection of charged chemical reaction products associated with the analyte. The amount of influence (field effects) can depend on, e.g., the strength of the charge, distance of field effect semiconductor from the charge, charge screening by other local charged molecules, and/or the dielectric character of the local environment. Analytes specifically or nonspecifically bound to the nanowire can provide strong field effects. Unbound analytes in the local environment (e.g., a charge cloud) can provide detectable field effects proportionate to their distance from the nanowire.

In some cases, the analyte of interest may comprise collections of ions that are not specifically associated with the nanowire component for detection, but which titrate groups on the surface of the nanowire or otherwise affect the environment of the nanowire in order to cause a change in an electrical parameter within the nanowire. For example, in some cases, e.g., separation of DNA species in a capillary electrophoretic system, separated bands of DNA will carry a charge cloud with them as they move in separate species bands along a channel or capillary. This charge cloud may generally be detected by the nanowire sensors of the invention as the cloud will affect the surface charge on the sample exposure region of the nanowire, e.g., by titrating or ionizing groups on that region, and thereby affecting the electrical parameters of the nanowire, e.g., resistivity.

Generally, a nanowire based sensor, e.g., a ChemFET sensor, typically employs a nanowire disposed between a source and drain electrode, and including an analyte exposure region, e.g., a portion of the nanowire between the source and drain that is subjected to the analyte material. The exposure region, as noted above may include specific binding moieties, e.g., that are complementary to a specific analyte of interest, or they may include non-specific reactive moieties, i.e., titratable groups, e.g., to detect charge changes in the analyte material, or hydrophobic or hydrophilic groups, or the like. Upon binding to the exposure region, a charged analyte imposes a field effect on the channel region of the subject nanowire altering an electrical characteristic of that nanowire between the source and drain, e.g., gating the current through the nanowire, which is then detected.

In accordance with certain aspects of the invention, and as set forth in greater detail below, individual binding events may only provide incremental shifts in the measured electrical parameters, and thus require longer incubation times to provide a sufficient number of binding events. Of course, in some cases signal drift through the nanowire, e.g., due to inconsistencies in electrical circuitry of the drive and detection electronics, evaporation or electrolysis of buffers, etc. can make identifying differences in binding levels difficult to accurately characterize. In such cases, a sudden separation of all analytes from the nanowire, and measurement of the resulting return of the nanowire to its original state, can be a better method of measuring the amount of binding. In particular, by utilizing a detection method that focuses on a relatively instantaneous return from the more fully bound nanowire to the unbound nanowire, one can minimize any accuracy problems associated with signal drift over time.

Figure 3A:
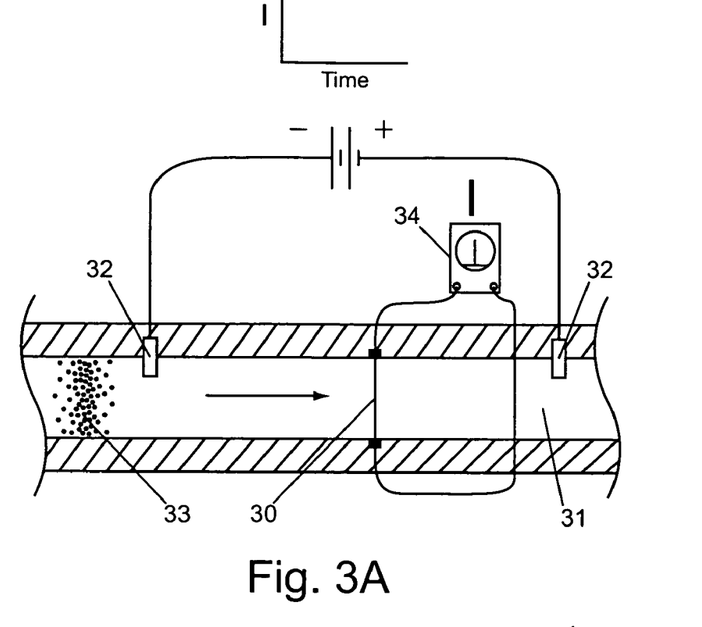
FIGS. 3A to 3D are schematic diagrams of a nanowire-based analyte sensor configured to detect the presence of an analyte in a channel.
Figure 3B:
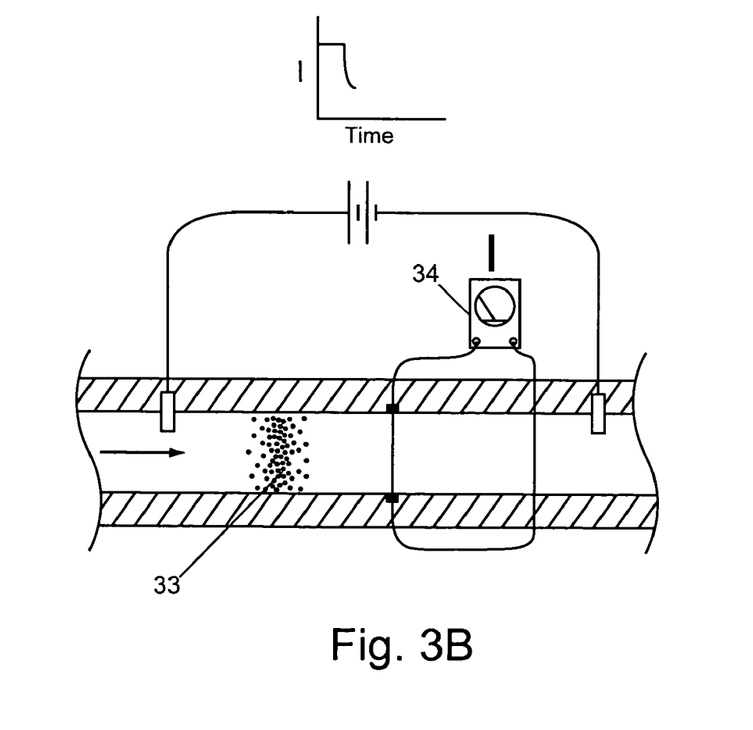
Figure 3C:
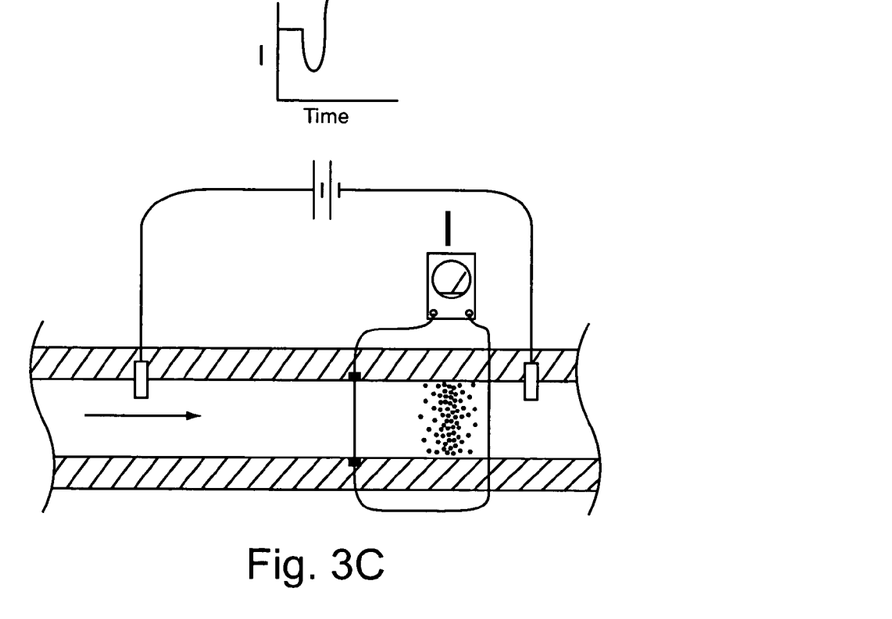
Figure 3D:
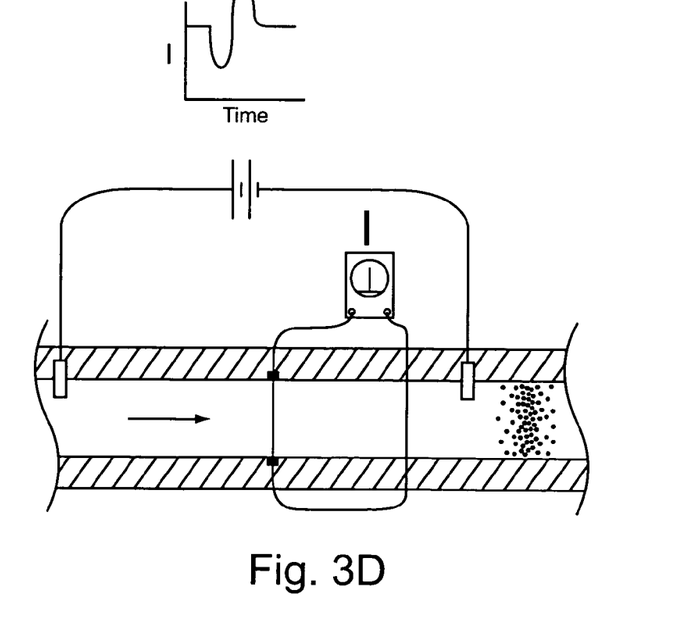

In one embodiment, analytes can cause detectable field effects, e.g., in a nanowire from some distance up or down a microchannel. For example, as shown in FIG. 3, a nanowire 30 can be mounted in channel 31 between source and drain electrodes 32 to provide a voltage potential along through the nanowire. Under initial conditions, as shown in FIG. 3A, with an analyte-free running buffer in the channel, a certain current flow can be detected by ammeter 34 in the n-type nanowire. As charged analyte 33 enters the channel between the voltage source electrodes, as shown in FIG. 3B, the electrical resistance of the upstream channel section can decrease (due, e.g., to the additional current carrying capacity provided by the analytes), subjecting the nanowire to a more negative voltage, repelling more carriers from the nanowire, and reducing current detected by ammeter 34. As the charged analyte passes into the microchannel downstream from the nanowire, as shown in FIG. 3C, the electrical resistance of the downstream channel decreases relative to the upstream section, subjecting the nanowire to a less negative voltage, repelling fewer carriers from the nanowire, and increasing current detected by the ammeter. Finally, when the wave of analyte has passed out of the channel section between the voltage source electrodes, as shown in FIG. 3D, the running buffer is again analyte-free, the voltage experienced by the nanowire returns to initial conditions, and detected current flow returns to initial levels. Such a sensor system can detect, e.g., the presence of an analyte in the channel, and provide signals for interpretation of analyte wave shape and/or the quantity of charged analyte present.

Figure 4A:
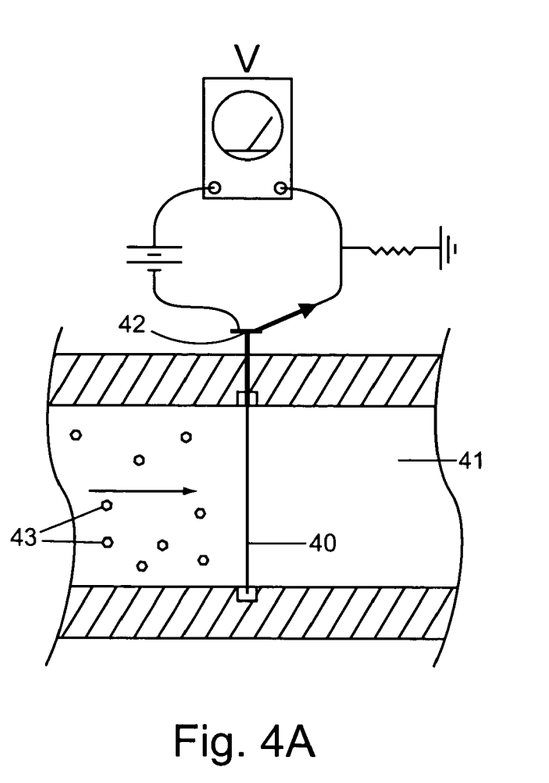
FIGS. 4A and 4B are schematic diagrams of a nanowire-based analyte sensor working in a piezojunction configuration.
Figure 4B:
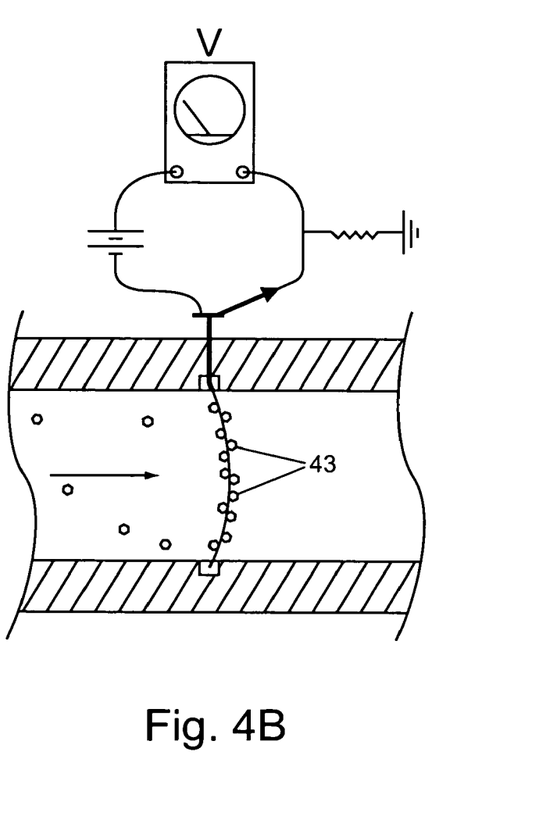

In another embodiment, analyte can be detected as stress transferred to a piezojunction at the base of a bipolar transistor. For example, as shown in FIG. 4, nanowire 40 is mounted across channel 41 under the stress of hydrodynamic drag from a fluid flowing in the channel. The nanowire is mounted on one side of the channel in association with piezojunction 42 of a bipolar transistor so that current flowing through the transistor is affected by tensile stress on the nanowire. The nanowire can have binding sites for analyte 43, which can build up, as shown in FIG. 4B, increasing hydrodynamic drag, increasing stress on the nanowire, increasing stress on the piezojunction, and ultimately changing the electrical current flowing through the transistor. The changed current can be detected, e.g., by an electrical parameter detector, such as a volt meter or ammeter, as is known by those skilled in the art.

To increase the specificity of detection and/or reduce the background signals to the detector, reference and/or control nanowires can be included in sensors of the invention. For example, where sensors employ nanowires with surface binding sites, a second nanowire without binding sites, or a nanowire located in an analyte-free running buffer, can be provided as a negative control for comparison purposes. In many cases, more precise comparisons can be made when the test and control nanowires are separate sections of the same original source nanowire; this is because nanowire sections from the same source can be more consistent in diameter and crystal character than nanowire sections from different source nanowires fabricated at another time. As nanowires can be fabricated in lengths well over 100 um, and microchannel mounted nanowires are often 20 um or shorter, a single source nanowire can provide several nanowire sections for use as test, reference and/or control nanowires.

Figure 5:
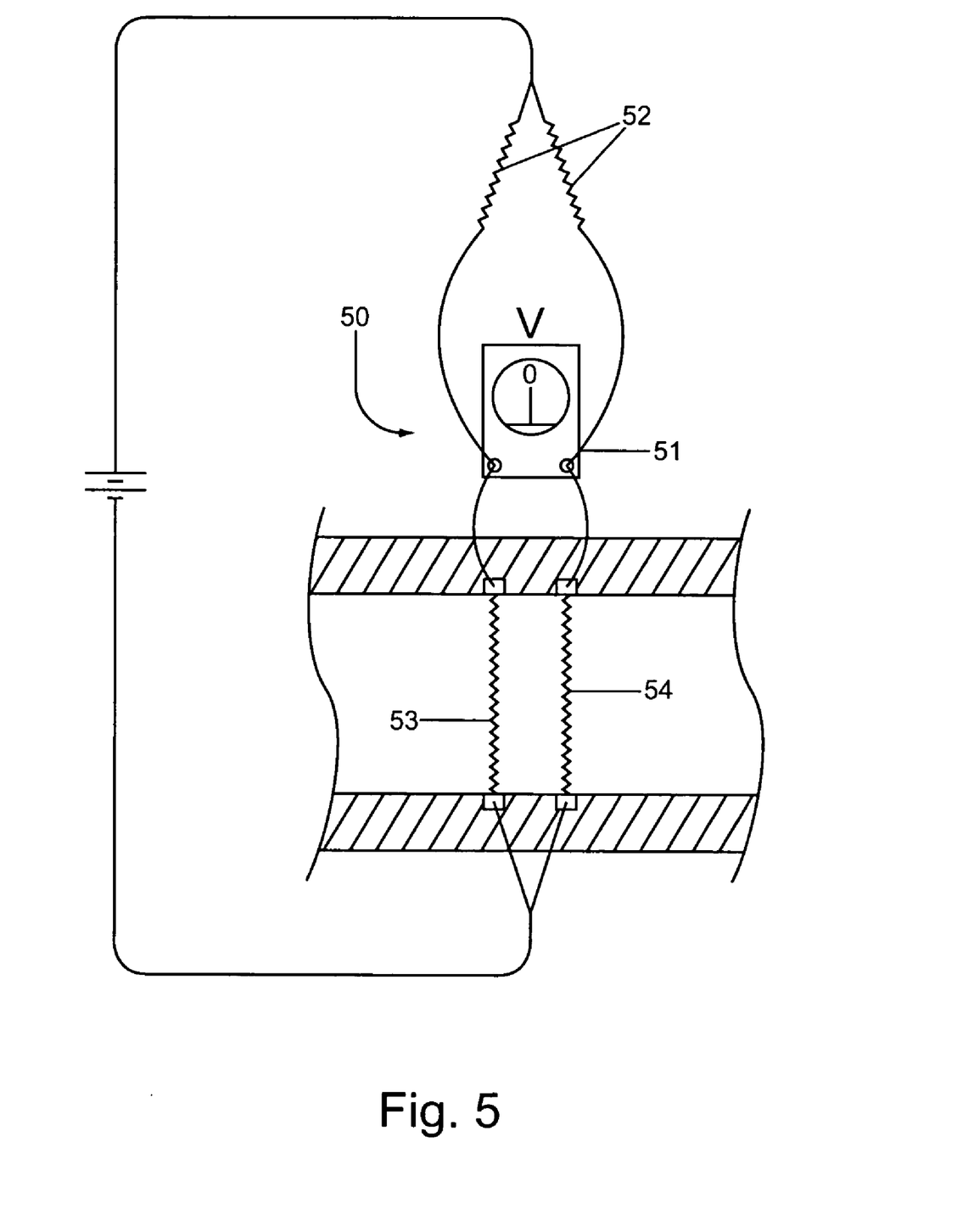
FIG. 5 is a schematic diagram of a nanowire-based analyte sensor in a Wheatstone bridge configuration including a negative control nanowire.

In embodiments of sensors where detection includes a comparison of resistance between two or more nanowires, a Wheatstone bridge circuit can enhance the sensitivity of the comparison, as is well known in the art. Wheatstone bridge 50, as shown in FIG. 5, is an electrical circuit for precise comparison of resistances, and highly sensitive detection of changes in resistance. In a Wheatstone bridge, voltage detector 51 bridges between resistors of a parallel circuit having two pairs of resistors in series. If two resistors 52 on one side of the bridge detector have the same resistance, two comparison resistors on the other side of the bridge can be compared with great sensitivity; any difference between the resistance of the comparison resistors will result in a voltage across the detector bridge greater than zero (note: a small change from zero voltage is easily detected).

In certain embodiments of the sensors, a Wheatstone bridge can be used to detect the presence of an analyte, even against a background of variable nonspecific signals. For example, as shown in FIG. 5, comparison resistors of a Wheatstone bridge can be test nanowire 53 and control nanowire 54. The nanowires are identical except for the test nanowire having a surface with specific binding sites and the negative control nanowire having no specific binding sites. During analysis for analyte by this setup, many variables are controlled. If molecules bind nonspecifically out of the microchannel fluid, they will do so to a similar extent on both the test and control wires to exert the same stress or field effect on both nanowires; thus reducing detection of false positive voltage signals. If flow rates in of the fluid in the channel change, a false positive will not be generated in a piezoelectric configured sensor because the changed hydrodynamic stress will be the same in test and control nanowires. If a bolus of high salt solution flows past the wires during an analysis, a false positive voltage will not be generated in a field effect configured sensor because the carrier repulsion and resistance to current flow will be the same for the test and control nanowires.

Methods of Sensing Analytes with Nanowire-Based Sensors

Methods of sensing analytes using nanowire-based sensors include, e.g., contacting nanowires mounted in a chamber with fluids containing the analyte, and detecting a change in an electrical parameter associated with the nanowire. The sensors can have a variety of configurations, as discussed in the Nanowire-Based Sensors section above. The nanowires can be mounted, e.g., by integral fabrication as part of a microchip, or by manipulation of the nanowires into selected electrical contacts. Contact of samples to nanowire sensors can be by, e.g., flow of the fluids within channels over the nanowires or by incubation of analytes with the nanowires within sample wells. Detection can include, e.g., measurement of nanowire associated electrical parameters by ammeters, volt meters, or ohm meters.

Mounting Nanowires in Microchambers

Mounting nanowires, as was described briefly in the Methods section above, can include, e.g., etching from a substrate, growing in situ, settling onto a masked surface, directing by flow orientation, micromanipulation, and/or the like. Mounting can provide, e.g., mechanical connections to transmit mechanical stresses to piezoelectric devices, and/or electrical connections to functionally associate nanowires of the methods with sensor circuits.

Nanowires can be mounted to microchamber surfaces by etching the nanowire from a substrate common to the chamber. Using photolithographic techniques, known in the art, nanowires can be fabricated, e.g., by etching a substrate according to a masked pattern. A layer of photoresist can be applied to the substrate, the photoresist exposed to a light source through a mask pattern, and the pattern disclosed by chemical dissolution of any photoresist not protected in the shadow of the mask. The patterned substrate can be etched by application of chemical etchants to the disclosed surfaces. A nanowire can remain, e.g., as the photoresist itself or as substrate protected from the etchant by the photoresist. Such a process can result in a strong mechanical and/or electrical connection between the nanowire and the substrate. Electrical circuitry and/or microchannels can be fabricated in the same process to provide a microfluidic device and/or circuit with an integrated nanowire sensor.

Nanowires can be grown in situ from a substrate such that, e.g., the origin of growth provides a mechanical and/or electrical connection between the nanowire and substrate. For example, sites can be precisely seeded on a substrate to grow nanowires from a selected location on the substrate. A wafer of silicon, or another substrate, can have a nanometer-scale gold particle, or other seed, located, e.g., by random dispersal, masking techniques, or micromanipulation. The substrate can be exposed to a vapor of a semiconductor material in a furnace so that semiconductor dissolves into the seed to concentrate and crystallize between the substrate and seed. A shaft of semiconductor crystal, about the same diameter as the seed can grow up from the substrate. Depending on the nature of the substrate, seed and semiconductor vapor, the nanowire and mounting connections can be endowed with electronic characteristics, such as piezoelectric effects, field effect sensitivity, and semiconductor junction (e.g., diode) quality. Dopants can be added, adjusted, and changed in the vapor to control the amount and/or type of carriers in the semiconductor. Adjusting the dopants as the nanowire grows can result in, e.g., a diode or transistor gate junction at or near the substrate mounting point, and/or extension of long piezoresistive or field effect sensitive nanowires out into a chamber.

Previously fabricated nanowires can be mounted to chamber surfaces, e.g., by settling, use of masks, flow orientation, and/or the like. Nanowires can be positioned, e.g., between points of contact across a channel by suspending nanowires in a fluid and allowing them to randomly settle across the contacts. A mask can be employed to prevent unwanted random connections. Proper nanowire orientation can be increased by flow orientation methods wherein a flow of fluid pushes nanowires in a desired direction. For example, nanowires made to roll along a surface will tend to orient with their axes perpendicular to the driving flow. In another example, nanowires with a nonuniformity, such as a bulbous end, can be made to orient parallel to a driving flow in a manner analogous to a weathervane. In another example, a nanowire grown from a substrate at a first mounting point can be pushed by a flow to contact a second mounting point by a directed flow of fluid. Fluids of flow orientation can be, e.g., liquids, gasses, or particles.

Nanowires can be positioned and mounted by micromanipulation. For example, nanowires held at the tips of manipulator probes capable of movement in three dimensions. The micromanipulator can be mounted on a vibration isolated stage with slidable tracks adjustable in three dimensions by the turning threaded micrometer shafts (in a fashion similar to microsurgery manipulators or neurophysiology probe manipulators). The turning can be motorized and/or controlled by computer systems. At a smaller scale, the manipulators can be, e.g., probes of scanning probe microscopy. Microscopes and/or camera technologies can be used to monitor manipulations. Once a nanowire is positioned, by whatever methods, permanent physical and/or electrical contact mounts can be prepared by, e.g., application of suitable chemistries, electric currents, light pulses, heat, and the like, to fuse the nanowires to the mounting points. Application of fusion energy or chemistry can be generalized, or focused in the mounting point, e.g., by micromanipulation.

Contacting Analytes to the Nanowires

Analytes in a fluid can come in contact with nanowires in the methods of the invention to, e.g., produce a change in an electrical parameter. Analytes can include, e.g., nucleic acids, antigens, antibodies, proteins, ions, and/or the like. Contact can include, e.g., incubation of the nanowire in the fluid or flow of the fluid over the nanowire. Contact can include, e.g., the presence of an analyte within the range of an electric field, non specific binding to the nanowire surface, or specific binding to sites on the nanowire surface.

Contact with a field effect sensitive nanowire can be, e.g., the presence of an analyte within a distance from which an analyte electric field can influence the amount of carriers in the nanowire. An analyte can exert field effect an influences without being bound to the wire. A significant factor in determining the distance over which the field effect can be exerted can be, e.g., the presence of other charged molecules in solution near the nanowire (charge screening). The effects of charge screening can be reduced by, e.g., lowering the ionic strength of buffers in the environment during detection of the analyte.

Binding of the charged analyte to the nanowire surface can provide a substantial field effect in the nanowire. With fewer charged molecules between the analyte and nanowire, charge screening can be reduced.

Binding of analyte to piezoelectric associated nanowires can provide a stress detectable as a change in an electrical parameter. Analytes of interest can bind non-specifically to nanowires to generate a piezoelectric signal. For example, a positively charged polymer in a fluid flow over a piezoresistant nanowire having negatively charged nonspecific binding sites can be captured to apply stress and cause a changed resistance in the nanowire. In another example, nucleic acids can be nonspecifically bound to a positively charged surface of a nanowire mounted to (or associated with) a piezojunction of a transistor to change the voltage or current passing through the transistor. Similar changes in electrical parameters can result from specific binding of analytes to specific binding sites on piezoresistant nanowires or nanowires mounted to piezojunctions.

Detecting Changed Electrical Parameters

Interaction of analytes with nanowires of the invention can result in detectable changes in electrical parameters. Piezosistance, piezojunction effects, and/or field effects can result in, e.g., detectable changes in electrical parameters such as voltage, resistance and current. Such electrical parameters can be detected, e.g., by volt meters, ohm meters, and/or ammeters. Detected changes in electrical parameters can be digitized for storage and interpretation by a computer system.

Tensile stress on a piezoresistive nanowire can change the electrical resistance in the nanowire. The nanowire mounting points in the chamber can be electrical contact points in a circuit with the detector. The detector can monitor resistance in the nanowire by detecting a changed voltage drop or current flow across the nanowire in response to the changed resistance. Typically, embodiments of the invention employing piezoresistive nanowires detect changes in resistance using an electrical parameter detector configured as an ohm meter.

As with the piezoresistive nanowire, a change in resistance or current can be detected when a field effect nanowire is in the presence of an analyte. For example, a nanowire in a field effect embodiment can be mounted to the chamber in electrical contact with a detector circuit. Charged analytes in the proximity of the nanowire, and/or bound to the nanowire, can influence the current carrying capacity of the nanowire. A change in current can be detected by an ammeter. The change in current carrying capacity can also be detected as a changed voltage drop by an electrical parameter detector configured as a voltmeter or ohm meter.

Tensile stress on a nanowire mounted to a piezojunction can change the voltage and/or current running through a transistor (piezotransistor) with a piezojunction gate. The detector can be in electrical contact, e.g., with an amplified signal from the piezotransistor. Typically, embodiments of the invention employing a piezojunction nanowire mount use a voltmeter or ammeter to detect the changed electrical parameter in response to increased hydraulic stress transmitted to the piezo junction.

The nanowire can be configured as a back gate to a field effect transistor. In such a case, the nanowire can be a field effect semiconductor integral to the transistor, or simply a binding site for charged analytes intimately associated with an FET. In any case, the field effects of the charged analytes can be monitored, e.g., by detectors in electrical contact with the amplification circuit of the transistor. Typically, embodiments of the invention employing a field effect nanowire mount use a volt meter or ammeter to detect the changed electrical parameter in response to the presence or binding of a charged analyte.

In certain embodiments, conditions of analytical separations can interfere with nanowire sensors. For example, when measuring analytes eluting from electrophoretic separations, or separations involving electroosmotic forces, voltages can interfere with detection of electrical parameters. Such interference can be avoided by turning off electrical currents during detection of the electrical parameters.

The ionic strength of solutions in the chambers of the invention can interfere with detection. For example, ions in strong salt solutions can cause charge screening that interferes with field effect detection methods of the invention. In another example, high ionic strength solutions can cause false positive field effects. In another example, high ionic strength solutions can cause increased nonspecific binding, such as low stringency nucleic acid hybridizations or hydrophobic interactions. In one aspect of the invention, the ionic strength of solutions in the chamber are reduced at the time of detection in order to lower such interference. In many cases, measurement of electrical parameters in low ionic strength solutions before exposure of nanowire sensors to analytes can enhance sensitivity by providing a negative control baseline comparison value.

In some embodiments of the invention involving specific or nonspecific binding, bound analytes can accumulate slowly. When binding of analytes is gradual, changed electrical parameters can be difficult to detect due to wandering of some detection circuits over time. One approach to addressing this problem can be, e.g., to accumulate bound analytes on the nanowire, then to detect changed electrical parameters as analytes are quickly removed from binding sites. For example, nucleic acids bound to complementary nucleic acid binding sites in the long hybridization can be quickly removed by a stringent washing buffer while changes in electrical parameters are detected. Alternatively, and often, preferably, a sudden increase in temperature can be employed to melt apart complementary nucleic acids, and thus free charged analyte from the detection or exposure region of the nanowire sensor element. Other removal schemes are also useful, including chemical treatment, e.g. enzymatic cleavage, photolytic cleavage of photoremovable linkages, or use of chaotropic agents, provided that such agents do not interfere with the detection event, e.g., by providing a highly charged buffer solution that may affect the nanowires electrical characteristics nonspecifically. The removal can be fast enough to avoid inaccuracies introduced by wandering of electronic circuits. The detector can measure an initial electrical parameter and an endpoint electrical parameter for calculation of the net change. Optionally, the detector can monitor the rate of change in an electrical parameter for kinetic evaluation of bound analyte. Removal of accumulated analytes can be by any appropriate means, such as application of ultraviolet light, heat, an enzyme, a wash solution, an electrical current, and/or the like.

Figure 6:
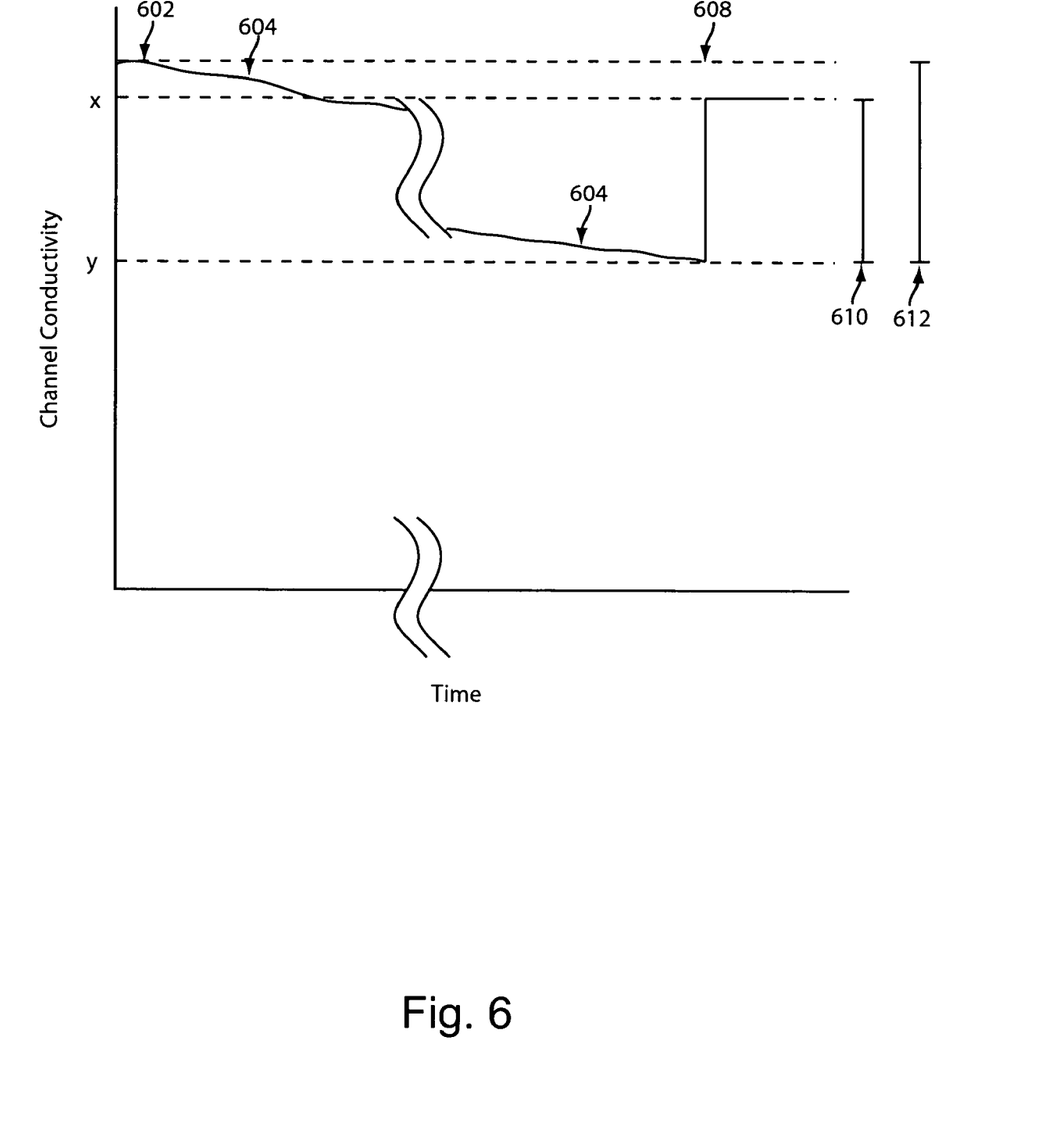
FIG. 6 is a schematic illustration of a hypothetical detection event using the post binding cleavage method of the present invention.

FIG. 6 schematically illustrates a plot of hypothetical data showing electrical current through a nanowire over time of a binding detection experiment. As can be seen, while the signal shifts over time in response to the binding event, the slope of the plot is relatively shallow, making the incremental changes much more difficult to monitor, and making the accuracy far more susceptible to signal drift issues. However, using an immediate cleavage based detection method a sharp indication of the amount of material bound to the nanowire sensor is provided as a sudden shift in the signal level that is directly attributable to the amount of analyte that had bound to, and was subsequently and suddenly removed from the nanowire sensor. In particular, and as shown, a nanowire sensor in the absence of an analyte provides a signal at level x. Upon introduction of a binding analyte at time point 602, the conductivity of the nanowire component begins to be gated by the binding events, although slowly, and provides a downward plotting line 604. Compounded with this gating effect is most likely some amount of signal drift associated with the system. After some length of time, the conductivity of the sensor has decreased to level y. At this point, the sensor is treated as described elsewhere herein, to remove any bound analyte from the nanowire sensor at time 608. The sudden release of analyte returns the nanowire to its original state, but including any artifactual drift associated with the system. As a result, the signal change that is a result of actual analyte binding normalized for any drift is shown as bar 610, as opposed to the artifactual result shown in bar 612.

In addition to the value of this approach to the accuracy of the data itself, it will be appreciated that such methods also benefit from an ability to preset experiments without lengthy monitoring requirements. In particular, one can preincubate a nanowire sensor with analyte of interest, and simply monitor the change in signal resulting from complete or near complete release of the analyte. As a result, the manpower, space and equipment requirements are substantially reduced.

Changed electrical parameters can be evaluated according to techniques well known in the art. For example, a reference analyte of known concentration can be titrated to validate the sensitivity (minimum signal above background for confident detection of the presence of an analyte) of an analyte detection method. In another example, the quantity of an analyte can be determined by comparison of the changed electrical parameter to a quantitative regression curve (standard curve) prepared from analysis of reference solutions with known analyte concentrations.

Multiple nanowires can be incorporated into sensors of the invention to provide controls for background noise and other nonspecific interference. For example, a nanowire without binding sites can be mounted in a microchamber to provide a nonspecific binding control for comparison to a test nanowire with specific binding sites. The control nanowire can provide control values, e.g., for electrical interference, pH effects, nonspecific field effects, nonspecific hydrodynamic drag effects, ion fluctuations, flow rate fluctuations, and/or the like. In some embodiments these effects can be reduced by treatment of the nanowire to block ion-exchange and/or pH sensitive sites. In one embodiment of the invention, the control nanowire and test nanowire are fabricated from the same source nanowire, thereby reducing variables associated with manufacture of the nanowires.

Multiple nanowires can be incorporated into sensors of the invention to increase the useful range of analyte detection. For example, multiple nanowires can be provided with different lengths, with different binding site densities, with different diameters, mounted in different locations, and/or the like. In embodiments of piezoresistive nanowire sensors, e.g., the length, diameter, and binding site density of nanowires can affect the sensitivity and quantitative range of analyte detection. Provision of multiple nanowires can, e.g., allow analysis of diverse samples without concentration or dilution to fit a relatively narrow analytical range of a single nanowire.

Multiple nanowires can be incorporated into sensors of the invention to provide multiple analyses of a single sample. For example, separate nanowires with binding sites for different analytes can be incorporated into one or more chambers on the same chip. One or more detectors can monitor the nanowires to detect the presence and/or quantity of multiple analytes from the same sample.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of detecting an analyte of interest, comprising:
providing a nanowire having a sample exposure region, the sample exposure region comprising at least one binding molecule for an analyte of interest disposed thereon, the nanowire being operably coupled to an electrical parameter detector;
contacting the sample exposure region with a sample material suspected of containing the analyte of interest for a first period of time to allow any analyte of interest in the sample material to associate with the sample exposure region of the nanowire;
treating the nanowire to rapidly remove at least a portion of the analyte of interest from association with the sample exposure region; and
monitoring the electrical parameter of the nanowire during at least the treating step and the removal of at least a portion of the analyte to detect a change in the electrical parameter of the nanowire in response to the treating step, the change in the electrical parameter being indicative of a presence or amount of the analyte of interest bound to the sample exposure region from the sample material.

2. The method of claim 1, wherein said treating the nanowire comprises exposing the nanowire to ultraviolet light to remove at least a portion of the analyte of interest from association with the sample exposure region.

3. The method of claim 1, wherein said treating the nanowire comprises exposing the nanowire to heat to remove at least a portion of the analyte of interest from association with the sample exposure region.

4. The method of claim 1, wherein said treating the nanowire comprises exposing the nanowire to an enzyme to remove at least a portion of the analyte of interest from association with the sample exposure region.

5. The method of claim 1, wherein said treating the nanowire comprises exposing the nanowire to a wash solution to remove at least a portion of the analyte of interest from association with the sample exposure region.

6. The method of claim 1, wherein said treating the nanowire comprises exposing the nanowire to an electrical current to remove at least a portion of the analyte of interest from association with the sample exposure region.

7. The method of claim 1, further comprising exposing the nanowire to a low ionic strength solution prior to monitoring the electrical parameter.

8. The method of claim 1, wherein the at least one binding molecule includes nucleic acids, peptite nucleic acids, antibodies, receptors, lectins, charged groups and/or chelators.

9. The method of claim 1, wherein the nanowire is piezoresistive, and wherein the change in the electrical parameter comprises a change in resistance of the piezoresistive nanowire.

10. The method of claim 1, wherein the nanowire exhibits an electrical field effect to provide a change in the electrical parameter.

11. The method of claim 10, wherein the nanowire is configured as a gate region in a transistor.

12. The method of claim 1, further comprising comparing the electrical parameter or the change thereof to that monitored for a control nanowire lacking the at least one binding molecule, and analyzing the comparison to determine background noise or other nonspecific interference.

13. The method of claim 1, wherein the electrical parameter is resistance.

14. The method of claim 1, wherein the electrical parameter is voltage.

15. The method of claim 1, wherein the electrical parameter is current.

16. A method of detecting an analyte of interest, comprising:
providing a nanowire having a sample exposure region, the sample exposure region comprising at least one binding molecule for an analyte of interest disposed thereon, the nanowire being operably coupled to an electrical parameter detector;
contacting the sample exposure region with a sample material suspected of containing the analyte of interest for a first period of time to allow any analyte of interest in the sample material to associate with the sample exposure region of the nanowire;
treating the nanowire to rapidly remove at least a portion of the analyte of interest from association with the sample exposure region; and
monitoring the electrical parameter of the nanowire during at least the treating step to detect a change in the electrical parameter of the nanowire in response to the treating step, the change in the electrical parameter being indicative of a presence or amount of the analyte of interest bound to the sample exposure region from the sample material.

17. The method of claim 16, wherein the electrical parameter is electrical resistance.

18. The method of claim 16, wherein the electrical parameter is resistance.

19. The method of claim 16, wherein the electrical parameter is voltage.

20. The method of claim 16, wherein the electrical parameter is current.

21. The method of claim 16, wherein the nanowire is configured as a gate region in a transistor.

22. The method of claim 16, wherein the treating step is done after a plurality of the analytes are bound to the nanowire.

* * * * *